United States Patent
Aljabab et al.

(10) Patent No.: US 12,310,812 B1
(45) Date of Patent: May 27, 2025

(54) MULTIFUNCTIONAL ORAL APPLIANCE

(71) Applicant: KING SAUD UNIVERSITY, Riyadh (SA)

(72) Inventors: Saif Abed Aljabab, Riyadh (SA); Abdullah Mohamed Alsoghier, Riyadh (SA); Abdurabu Abdullah Gomawi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/611,014

(22) Filed: Mar. 20, 2024

(51) Int. Cl.
*A61C 7/08* (2006.01)
*A61F 2/82* (2013.01)
*A61N 5/00* (2006.01)

(52) U.S. Cl.
CPC ............... *A61C 7/08* (2013.01); *A61F 2/82* (2013.01); *A61N 5/00* (2013.01)

(58) Field of Classification Search
CPC ......... A61C 7/08; A61C 19/06; A61C 19/063; A61F 2/82; A61N 5/00
See application file for complete search history.

(56) References Cited

U.S. PATENT DOCUMENTS

| | | | | |
|---|---|---|---|---|
| 5,842,860 | A * | 12/1998 | Funt | A61J 7/0092 433/80 |
| 6,247,930 | B1 * | 6/2001 | Chiang | A61C 19/063 433/80 |
| 9,504,537 | B2 * | 11/2016 | Johnson | A61N 5/10 |
| 10,363,004 | B2 * | 7/2019 | Holman | A61C 9/0053 |
| 2009/0209852 | A1 | 8/2009 | Mate et al. | |
| 2010/0028829 | A1 | 2/2010 | Lewis et al. | |
| 2012/0012120 | A1 * | 1/2012 | Giffey | A61B 13/00 128/859 |
| 2012/0231412 | A1 * | 9/2012 | Sirjani | A61C 19/063 433/89 |
| 2018/0153485 | A1 | 6/2018 | Rahmes et al. | |
| 2019/0151042 | A1 * | 5/2019 | Holman | A61N 5/1047 |
| 2020/0170749 | A1 | 6/2020 | Koay et al. | |
| 2020/0281970 | A1 | 9/2020 | Burd | |
| 2022/0304786 | A1 * | 9/2022 | Ciesicki | A61C 19/06 |
| 2022/0354629 | A1 | 11/2022 | Ehrenpreis | |

* cited by examiner

*Primary Examiner* — Ralph A Lewis
(74) *Attorney, Agent, or Firm* — Nath, Goldberg & Meyer; Joshua B. Goldberg

(57) ABSTRACT

A method and device using a multifunctional oral appliance is provided with the capabilities of protecting healthy tissue during a radiotherapy treatment for oral cancers. The multifunctional oral appliance includes a reservoir for holding medications, moisturizing liquids, and other drugs required during treatment. The multi-functional oral appliance also includes a separate element for positioning of the tongue during a radiotherapy treatment.

7 Claims, 9 Drawing Sheets

MULTIFUNCTIONAL ORAL APPLIANCE

BACKGROUND

1. Field

The present disclosure relates to intraoral stents for radiotherapy when deployed in a collaborative effort involving radiation oncologists, oral and maxillofacial surgeons, and radiation therapists. The stents are carefully designed and fabricated based on individual patient needs and treatment plans. Close monitoring and assessment are essential throughout treatment to ensure proper positioning and optimal outcomes.

2. Description of the Related Art

Radiotherapy will continue to play a significant role in the treatment of malignant tumors of the head and neck. But this comes at the cost of severe side effects such as dry mouth, pain, difficulty swallowing, weight loss, fatigue, loss of appetite, and dermatitis. Radiation also causes long-term side effects such as loss of the sense of taste and smell, difficulty speaking and swallowing, dry mouth, and difficulty hearing, along with many other side effects which significantly affect patients' quality of life.

Despite these side effects, radiotherapy is an integral part of treatment for these patients and cannot be avoided in most cases. Many recent studies have attempted to reduce radiotherapy's side effects burden. This includes improved radiotherapy technology and special devices such as custom oral stents.

The role of custom oral stents is to provide some stability in the oral cavity and help deflect the tongue from the radiotherapy field. To date, many different types of oral stents are available in the market, and they all play different roles, making it difficult to choose between them, let alone adhere to them during treatment.

Oral cancer refers to the development of malignant tumors in the oral cavity, which includes the lips, tongue, gums, inner lining of the cheeks, the floor of the mouth, and the hard and soft palate. Head and neck cancer (HNC) is a broader term that encompasses cancers arising in various structures of the head and neck region, including the oral cavity, throat (pharynx), voice box (larynx), nasal cavity, and sinuses.

The primary risk factors for developing oral and head and neck cancer include tobacco use (e.g. cigarettes, cigars, smokeless tobacco), excessive alcohol consumption, exposure to human papillomavirus (HPV) infection, prolonged sun exposure (lip cancer), and a history of previous head and neck cancer. Additionally, certain dietary factors, poor oral hygiene, chronic irritation, and a compromised immune system may also contribute to the development of these cancers.

Managing oral and head and neck cancer depends on factors such as stage and location, the tumor characteristics (e.g. T and N stage, site of the primary tumor, tumor differentiation, involved margins of resection, extracapsular spread, perineural invasion), the patient's overall health, and personal preferences. Management options often include surgery to remove the tumor and radiation therapy. Also, chemotherapy, targeted therapy, or a combination of these modalities might be considered. The objectives of management include eradicating or controlling cancer while preserving essential functions such as speech, swallowing, and appearance.

Oral cancer and HNC and their management can significantly impact a person's life's physical, emotional, and social aspects. Functional impairment can occur due to surgical removal of tumors or radiation-related side effects such as difficulty swallowing (dysphagia), speech problems, and changes in taste or salivary function. Psychological support, rehabilitation programs, speech therapy, dental interventions, and counseling can help patients manage these challenges and improve their quality of life.

Radiotherapy (RT) is an often-used treatment modality for oral cancer, aimed at eradicating cancer cells and preventing their further growth. While RT can effectively control or eliminate cancer, it can also lead to various adverse effects specific to the oral cavity, with its severity being determined by factors such as the radiation dose, treatment duration, patient characteristics, and other underlying medical conditions. For instance, oral mucositis is one of radiotherapy's most prevalent side effects. It involves inflammation and ulceration of the oral mucous membranes and causes pain, redness, swelling, and oral ulceration. Thus, it can significantly impact a patient's ability to eat, drink, and speak comfortably.

Furthermore, xerostomia (oral dryness) occurs when the salivary glands are affected by RT, reducing saliva production. Saliva plays a crucial role in oral health by lubricating the oral cavity, facilitating swallowing and speech, and protecting against dental decay. Xerostomia can cause discomfort, difficulties in eating and speaking, an increased risk of dental problems, and altered taste sensations. Also, RT to the oral cavity can affect taste buds and lead to changes in taste perception leading to a metallic or bitter taste in the mouth or a loss of taste sensation.

Moreover, RT to the oral region can increase susceptibility to dental caries (rampant caries) due to the reduced saliva flow and changes in oral pH create an environment conducive to tooth decay. These adverse effects of RT can significantly impact the physical, emotional, and social well-being and quality of life of patients with HNC. Physical challenges can affect a patient's ability to eat, communicate, and perform daily activities, leading to a decline in overall well-being.

Multidisciplinary healthcare teams, including oncologists, radiation oncologists, dentists, speech therapists, nutritionists, and psychologists, often collaborate to provide holistic care and address the diverse needs of patients. Each patient's experience and quality of life will be unique. Therefore, open communication, personalized care plans, and a robust support system are vital to improving the quality of life during RT for HNC.

Management and support for xerostomia caused by radiotherapy involve several approaches to alleviate symptoms and enhance oral comfort, including oral hydration and using saliva substitutes or oral moisturizers. Dental fluoride interventions are also recommended for patients with xerostomia resulting from radiotherapy using fluoride gels, varnishes, or foams to help strengthen tooth enamel and provide extra protection against dental caries.

Intraoral stents for RT are specialized devices used to optimize the delivery of radiation treatment for oral cancers. These stents are designed to be placed inside the patient's mouth, providing a stable and reproducible position for accurate radiation targeting while minimizing the radiation dose to surrounding healthy tissues and assisting a precise targeting of radiation while reducing the potential damage to adjacent normal tissues (tongue), alveolar bone and parotid salivary glands. This was found to reduce the grade of OM and its management with opioids, trismus, xerostomia, dysgeusia (taste dysfunction), and osteoradionecrosis of the jaw without perhaps affecting the target dosage to control a tumor. Intra-oral RT stents can be used for shielding, as a radiation carrier, or as a positioning appliance, depending on the targeted site and RT delivery system.

Intraoral stents are typically custom-made for each patient based on their anatomical features. They are usually constructed from biocompatible materials, mostly acrylic resin, medical-grade silicone, thermoplastic materials, polyethylene terephthalate, and silicone. Such stents are often carefully designed to fit snugly inside the patient's mouth, ensuring stability during radiotherapy sessions.

Another crucial aspect of intraoral stents is their ability to shield and protect healthy structures during radiotherapy. By placing the stent in strategic positions, critical organs and tissues surrounding the tumor can be shielded from excessive radiation exposure. This feature helps to mitigate potential side effects and complications that may arise from irradiation of healthy tissues, such as xerostomia (dry mouth), mucositis, and damage to the salivary glands. Additionally, intraoral stents may incorporate features to improve treatment planning and delivery. For example, they can have radiopaque or fiducial markers embedded within them, aiding in precise visualization and alignment of the tumor during imaging and treatment sessions. This enables more accurate targeting and ensures that the radiation is delivered to the intended area.

The use of intraoral stents for radiotherapy is a collaborative effort involving radiation oncologists, oral and maxillofacial surgeons, and radiation therapists. The stents are carefully designed and fabricated based on individual patient needs and treatment plans. Close monitoring and assessment are essential throughout treatment to ensure proper positioning and optimal outcomes.

As such, intraoral stents for radiotherapy are specialized devices that contribute to the effective treatment of oral cancers. By immobilizing the patient's mouth, shielding healthy tissues, and facilitating accurate targeting, these stents help enhance the precision and safety of radiation therapy. Their customization and integration into treatment planning make them valuable tools in the fight against oral cancer.

What is needed is a method and device of a new customizable oral prop that combines multiple functions while being deployed as an oral stent for using radiotherapy to treat oral cancers in patients.

SUMMARY

The present subject matter is directed towards a method and device using an intraoral stent for radiotherapy in the treatment of oral cancer.

In a first aspect, the present subject matter relates to a device that is an oral stent comprising two pieces, a first piece that fits over the upper jaw, and a second piece that fits over the lower jaw. Each piece is generally arcuate in shape with curvatures matching the shape of the upper and lower rows of teeth, such that the first piece fits over the upper row of teeth and the second piece fits over the lower row of teeth in a patient's jaw. The first piece of the oral stent can also include a reservoir. A separator can also be provided between the first piece and the second piece to provide a gap of separation between the two pieces as the point insertion of the separator. The oral stent can also include an upper jaw teeth ridge for the first piece and a lower jaw teeth ridge for the second piece. And lastly, the device of the oral stent can also include a fin shaped tongue deviation septum for positioning the tongue during the radiotherapy treatment.

A second aspect of the present subject matter relates to an oral stent comprising two pieces, a first piece that fits over the upper jaw, and a second piece that fits over the lower jaw. Each piece is generally arcuate in shape with curvatures matching the shape of the upper and lower rows of teeth, such that the first piece fits over the upper row of teeth and the second piece fits over the lower row of teeth in a patient's jaw. The first piece of the oral stent can also include a reservoir. A separator can also be provided between the first piece and the second piece to provide a gap of separation between the two pieces as the point insertion of the separator. In this instance the point of separation can be provided at one side of the patient's mouth rather than in the front. The oral stent can also include an upper jaw teeth ridge for the first piece and a lower jaw teeth ridge for the second piece. And lastly, in this embodiment, the device of the oral stent can also include a flap shaped tongue deviation septum for positioning the tongue inferiorly away from the radiation field during the radiotherapy treatment.

A third aspect of the present subject matter relates to a method of using an oral stent as described herein during a radiotherapy treatment.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF EMBODIMENTS

Figure 1:
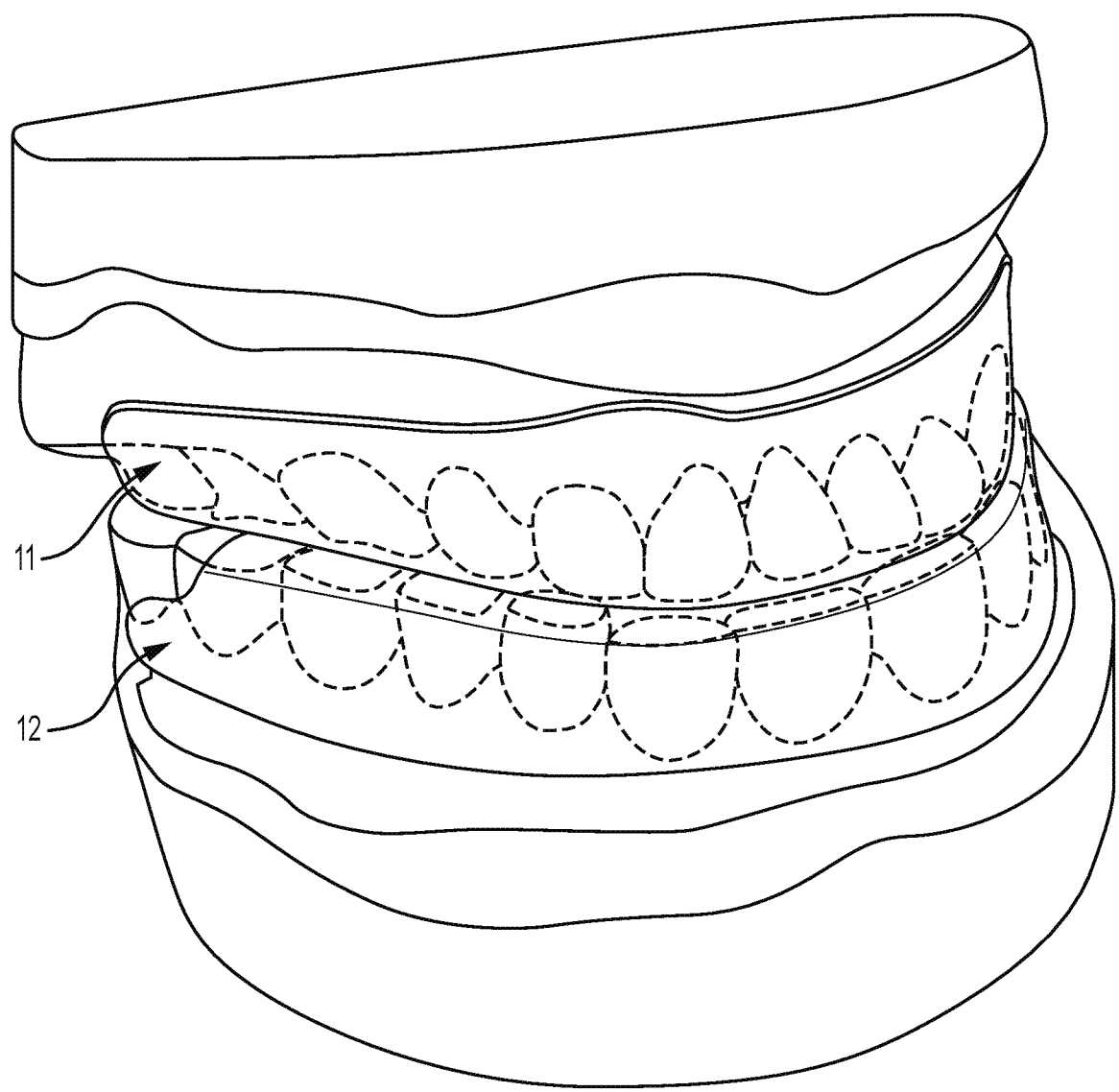
FIG. 1 is an overall view of a first embodiment of the multi-functional oral stent.
Figure 2:
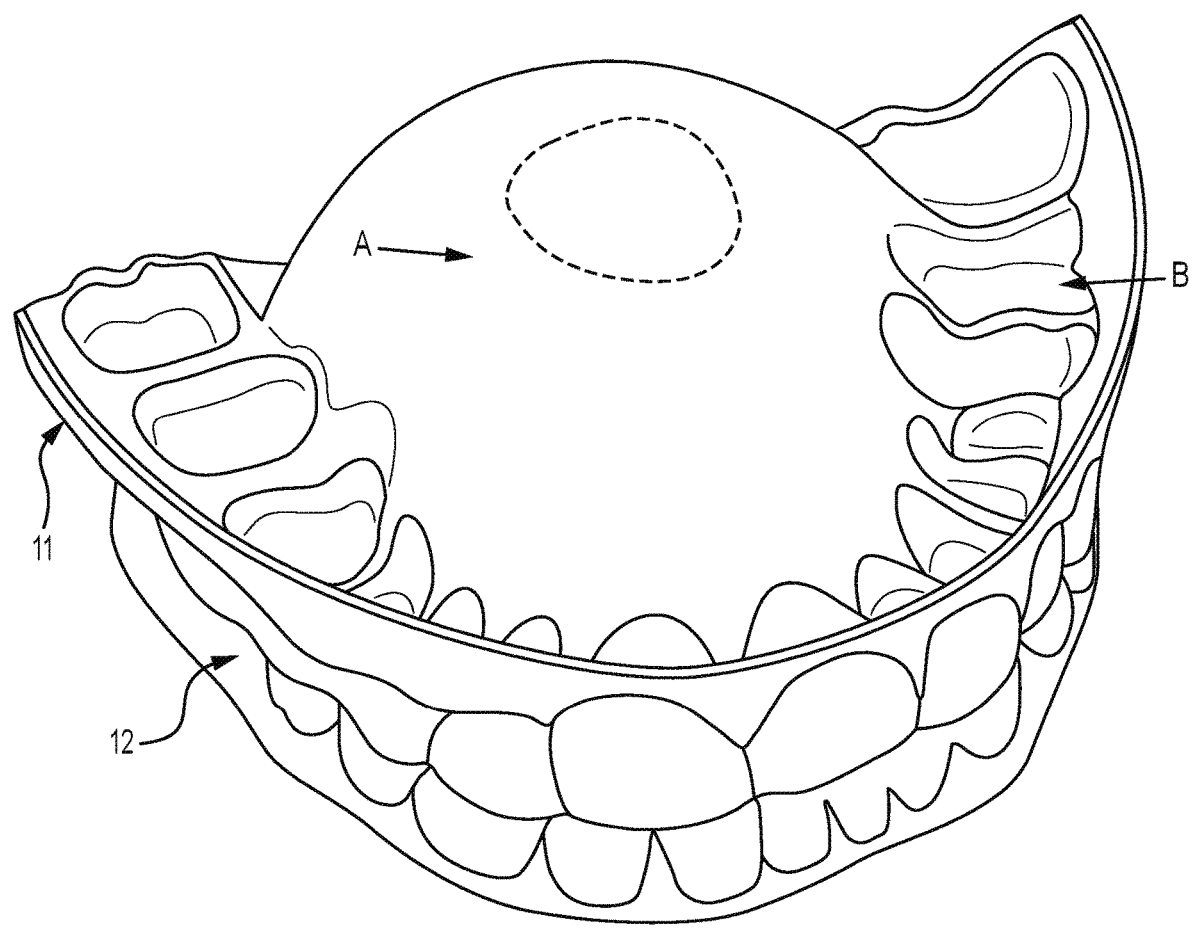
FIG. 2 is a superior (top) view of the first embodiment of the multi-functional oral stent.
Figure 3:
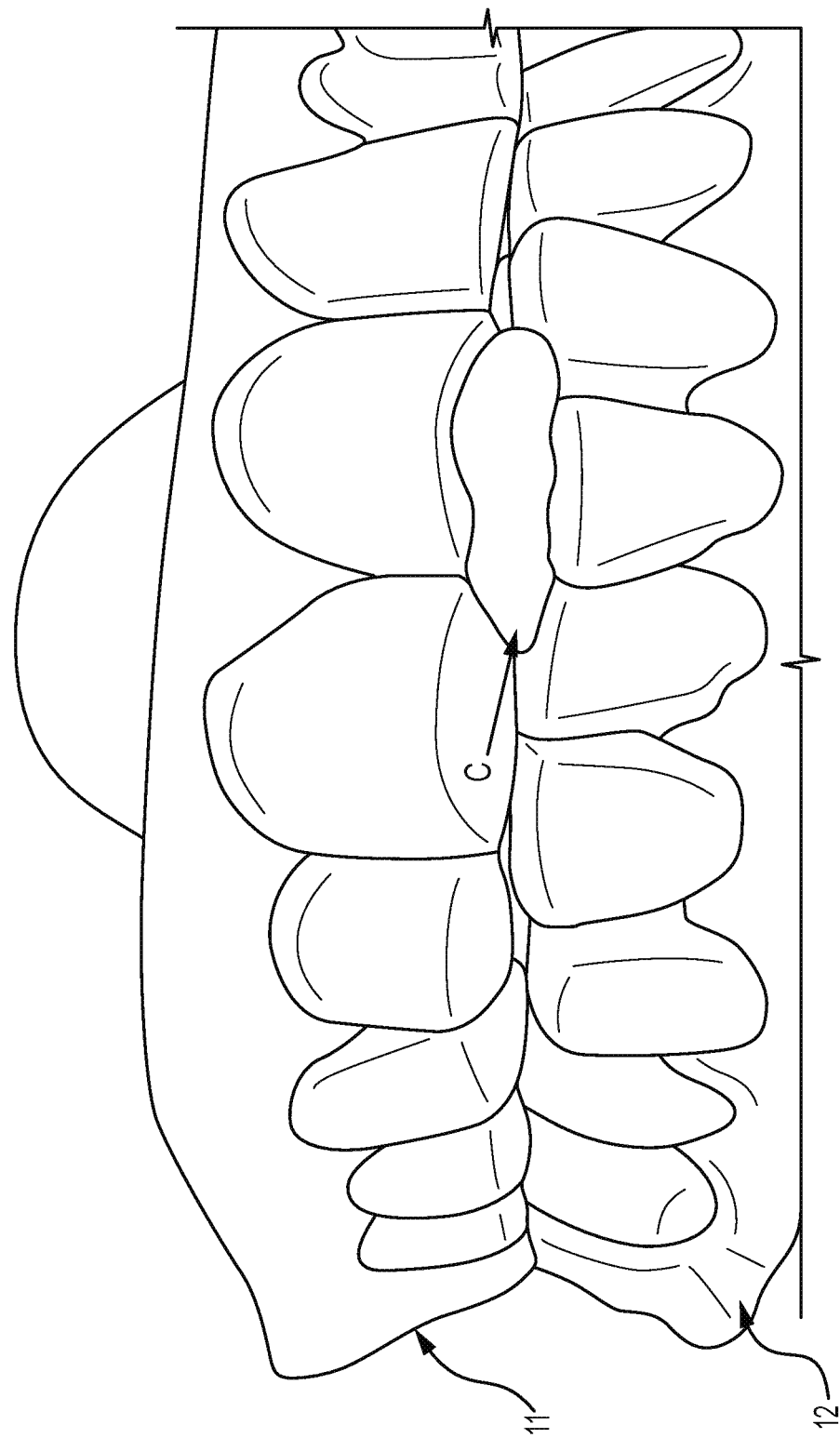
FIG. 3 is a frontal view of the first embodiment of the multi-functional oral stent.
Figure 4:
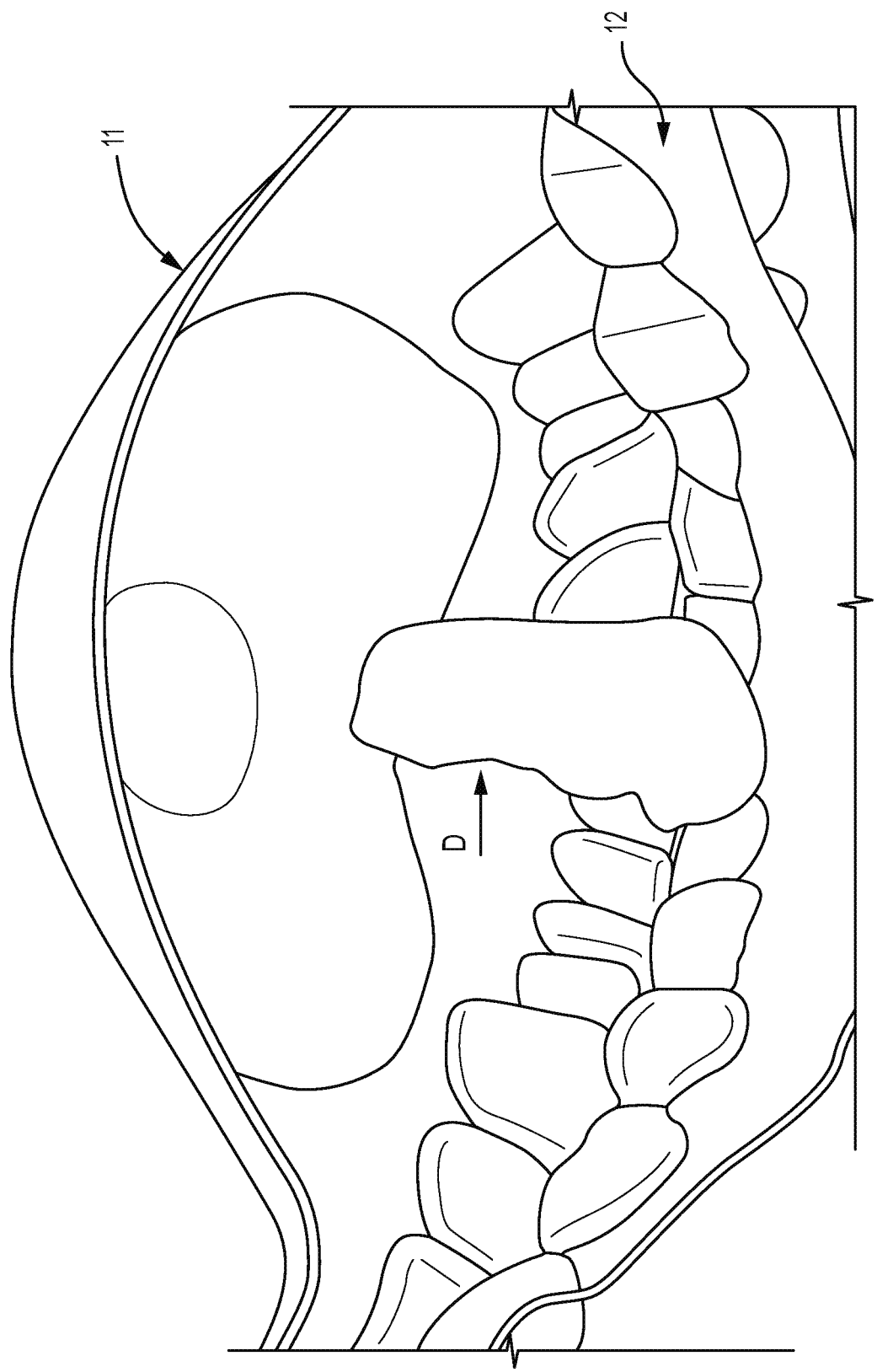
FIG. 4 is a rear view of the first embodiment of the multi-functional oral stent.
Figure 5:
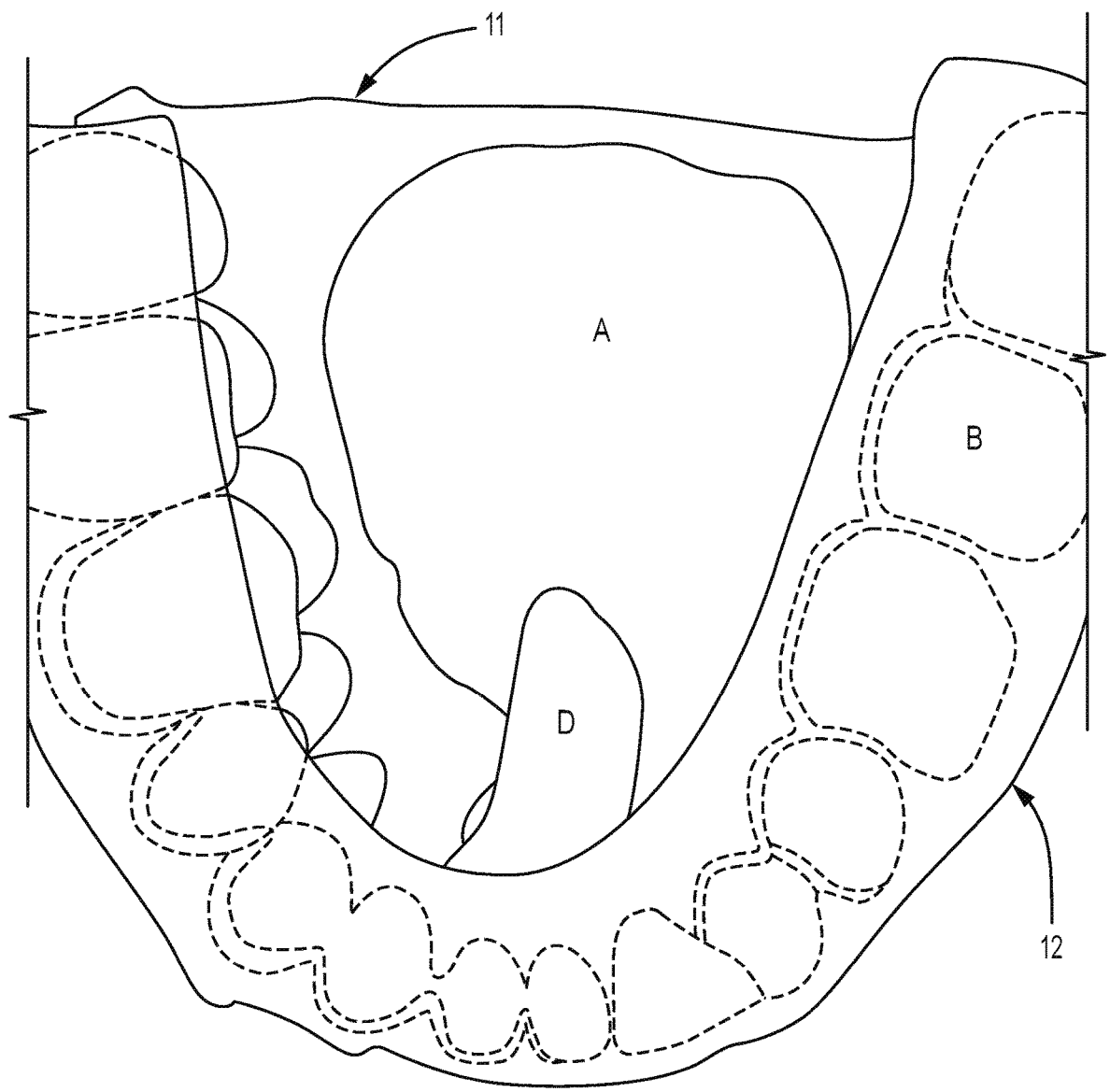
FIG. 5 is an inferior (bottom) view of the first embodiment of the multi-functional oral stent.
Figure 6:
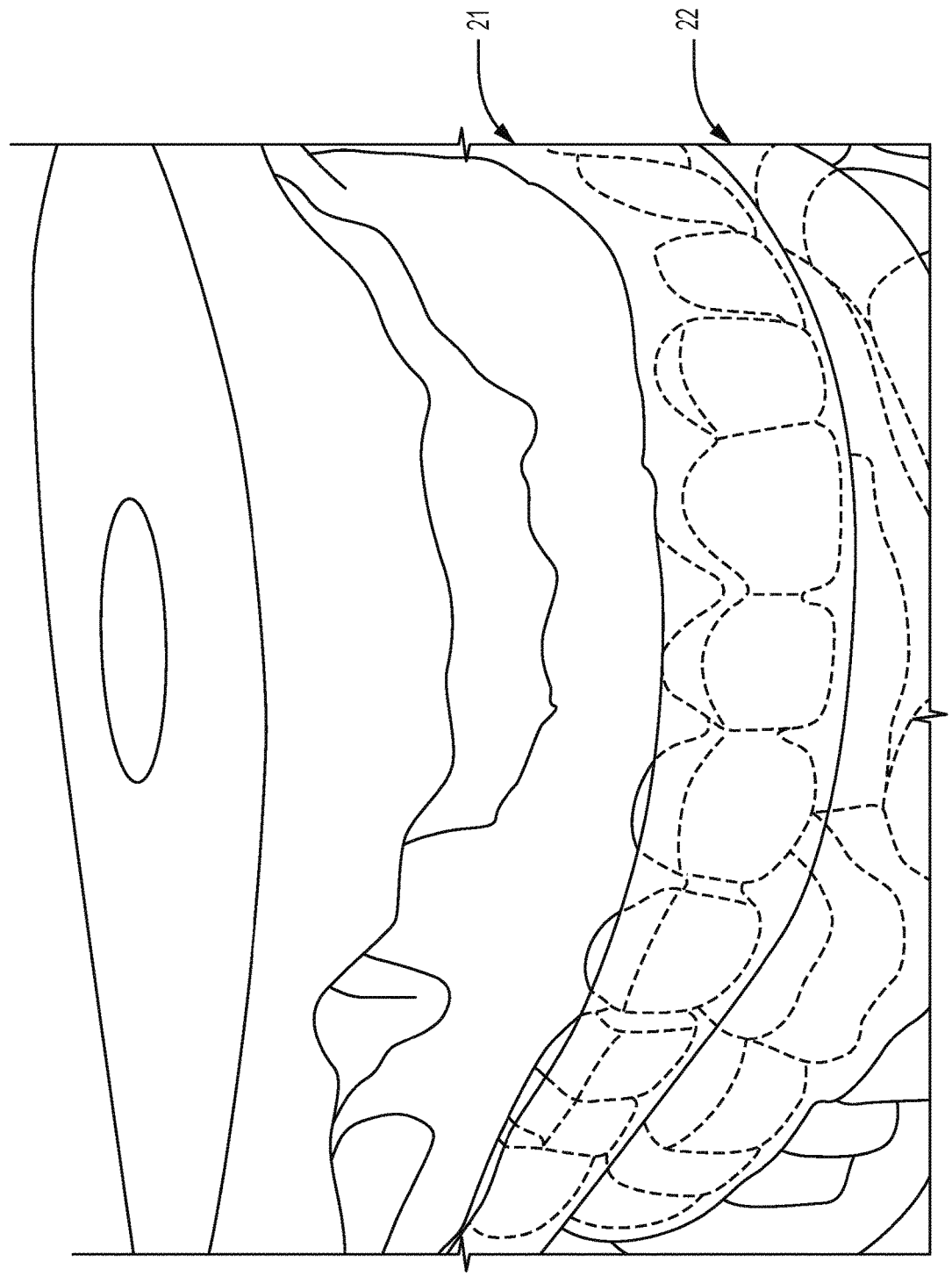
FIG. 6 is an overall view of a second embodiment of the multi-functional oral stent.
Figure 7:
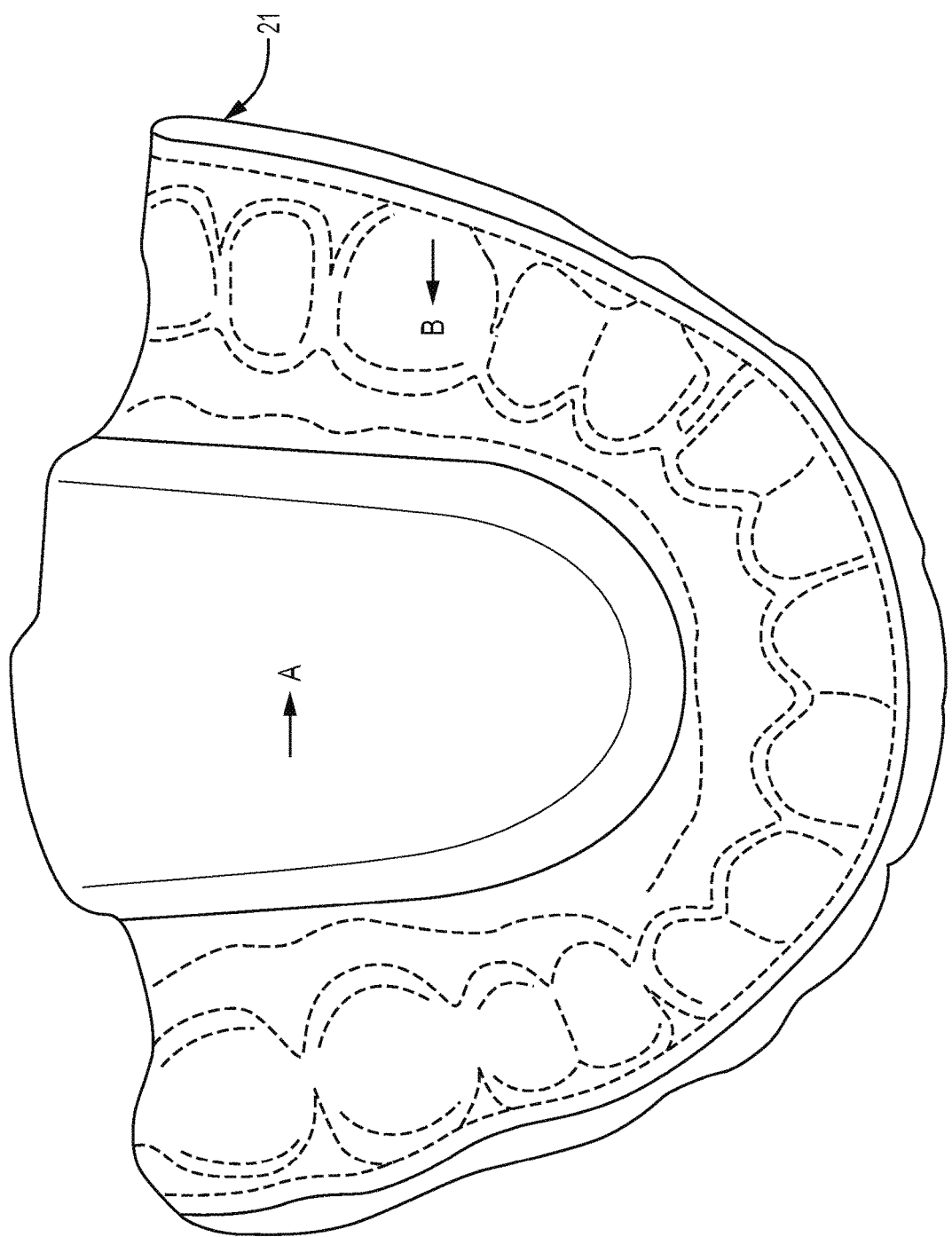
FIG. 7 is a superior (top) view of the second embodiment of the multi-functional oral stent.

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the concepts defined in the appended claims. Hence, specific dimensions and other physical characteristics relating to the embodiments disclosed therein are not to be considered as limiting, unless the claims expressly state otherwise.

Definitions

Throughout the application, where devices are described as having, including, or comprising specific components, or where processes are described as having, including, or comprising specific process steps, it is contemplated that the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Patient" as used herein refers to a subject in need of treatment.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the oral stents as described herein can consolidate four functions that no other oral appliance provides during the administering of a treatment during radiotherapy. These oral stents can serve as a tongue depressor and teeth protector from radiation, and can further include custom-made radiation shields for healthy tissue protection. The present stents can also provide tongue immobilization and bite protection devices helpful during the administration of RT to reduce the radiation scattering to soft tissues and teeth. In addition, the oral stents can also act as salivary substitute reservoirs or fluoride vehicles sought as necessary during RT to improve the treatment outcomes and reduce oral health-related morbidities during and after RT.

The newly designed oral stent can be cost-effective for its combined function with simple fabrication steps using one or more of acrylic resin, poly (methyl methacrylate), polyurethane, co-polymers of vinyl acetate or ethylene, polyvinyl acetate-polyethylene, ethylene vinyl acetate (EVA) copolymer, polyvinylchloride, latex rubber, silicon rubber, and/or other laminated or non-laminated thermoplastics in any dental laboratory. The fabrication of this new appliance was adapted with modifications of conventionally known construction processes.

First, the oral stent can be constructed based on the standard impression tray using alginate or a 3D scanning method developed from a standard computer tomography (CT) segmentation method. Mixed ordinary plaster can be poured into a mold and left to set until completely firm, leading to a force plug. Then, the plaster plug can be coated with a softened rigid polyester film, for example, having a thickness of about 2 mm (Thermoforming plates, Dreve-Dentamid GmbH, Germany) using a vacuum lamination machine. After being trimmed and released, the oral stent can be prepared. Several fixed holes with an inner diameter of about 2 to about 4 mm can be made to fasten silicon rubber with a sanding kit. According to the size of the impression tray, small, medium and large types of oral stents can be produced, to accommodate differing mouth sizes of different patients. The height of the oral stents can range from about 1 cm to about 3 cm. A general configuration of the oral stent can comprise four parts: upper alveolus 11, lower alveolus 12, tongue depressor plates D, and fixed holes. The oral stents can be used as rigid containers for carrying silicon rubber into the mouth, for maintaining it in position during setting or hardening, and supporting it.

As depicted in FIGS. 1-5, a first embodiment relates to an oral stent device comprising three pieces, a first piece 11 corresponding to the upper alveolus that fits over the upper jaw, a second piece 12 corresponding to the lower alveolus to the that fits over the lower jaw, and a fin shaped tongue deviation septum D. Each piece can be generally arcuate in shape with curvature matching the shape of the upper and lower rows of teeth, such that the first piece 11 fits over the upper row of teeth by aligning with an upper jaw teeth ridge B in FIG. 2, and the second piece 12 fits over the lower row of teeth by aligning with a lower jaw teeth ridge B in FIG. 5, in a patient's jaw. The first piece 11 of the oral stent can also include a reservoir A. Reservoir A can be used to hold a required amount of medication, moisturization liquids, and/or other forms of drugs to be placed therein during treatment. A separator C is also provided between the first piece 11 and the second piece 12 to provide a gap of separation between the two pieces as the point insertion of the separator C. And lastly, the third piece of the device of the oral stent is a fin shaped tongue deviation septum D for positioning the tongue during the radiotherapy treatment.

Figure 8:
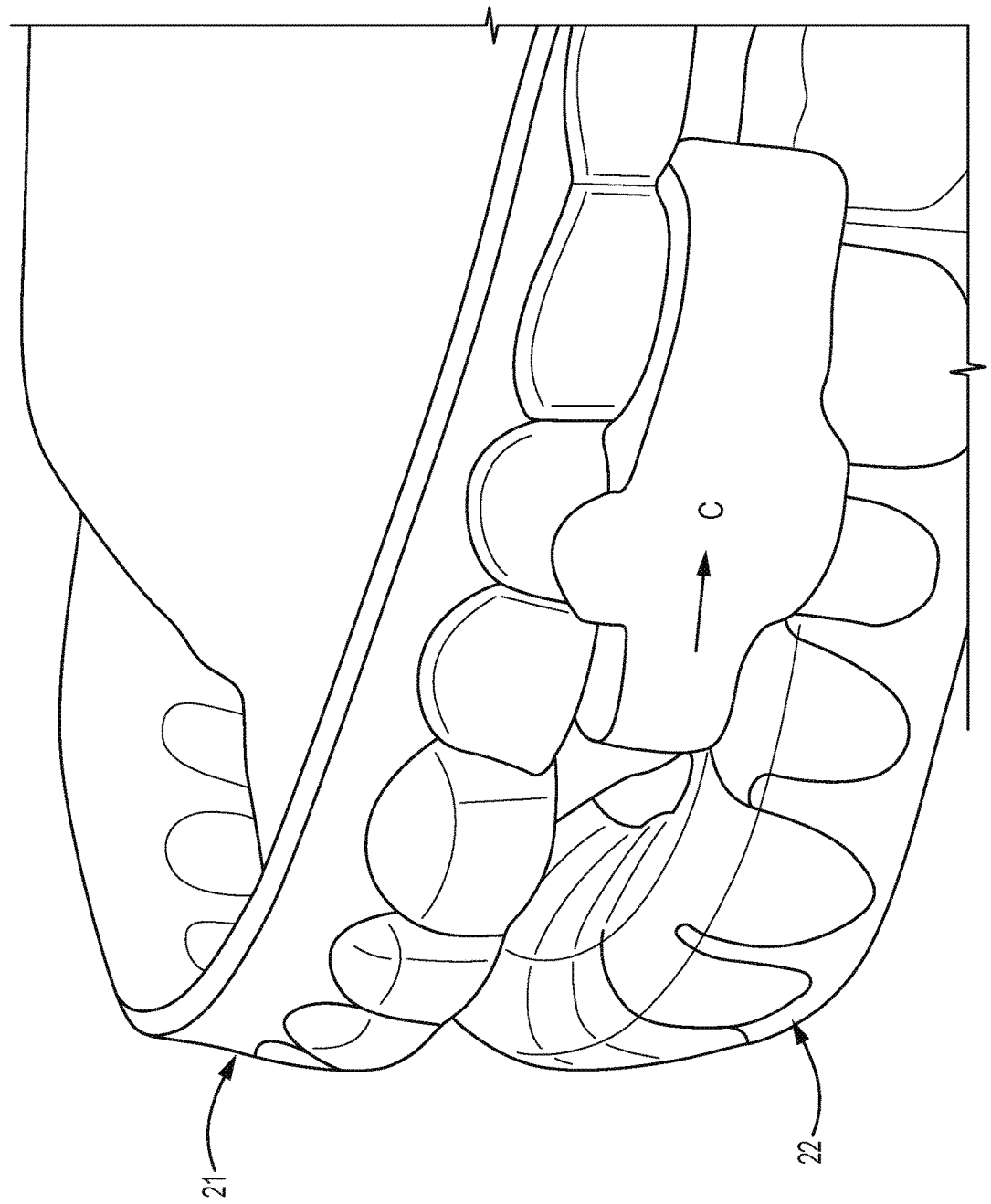
FIG. 8 is a side view of the second embodiment of the multi-functional oral stent.
Figure 9:
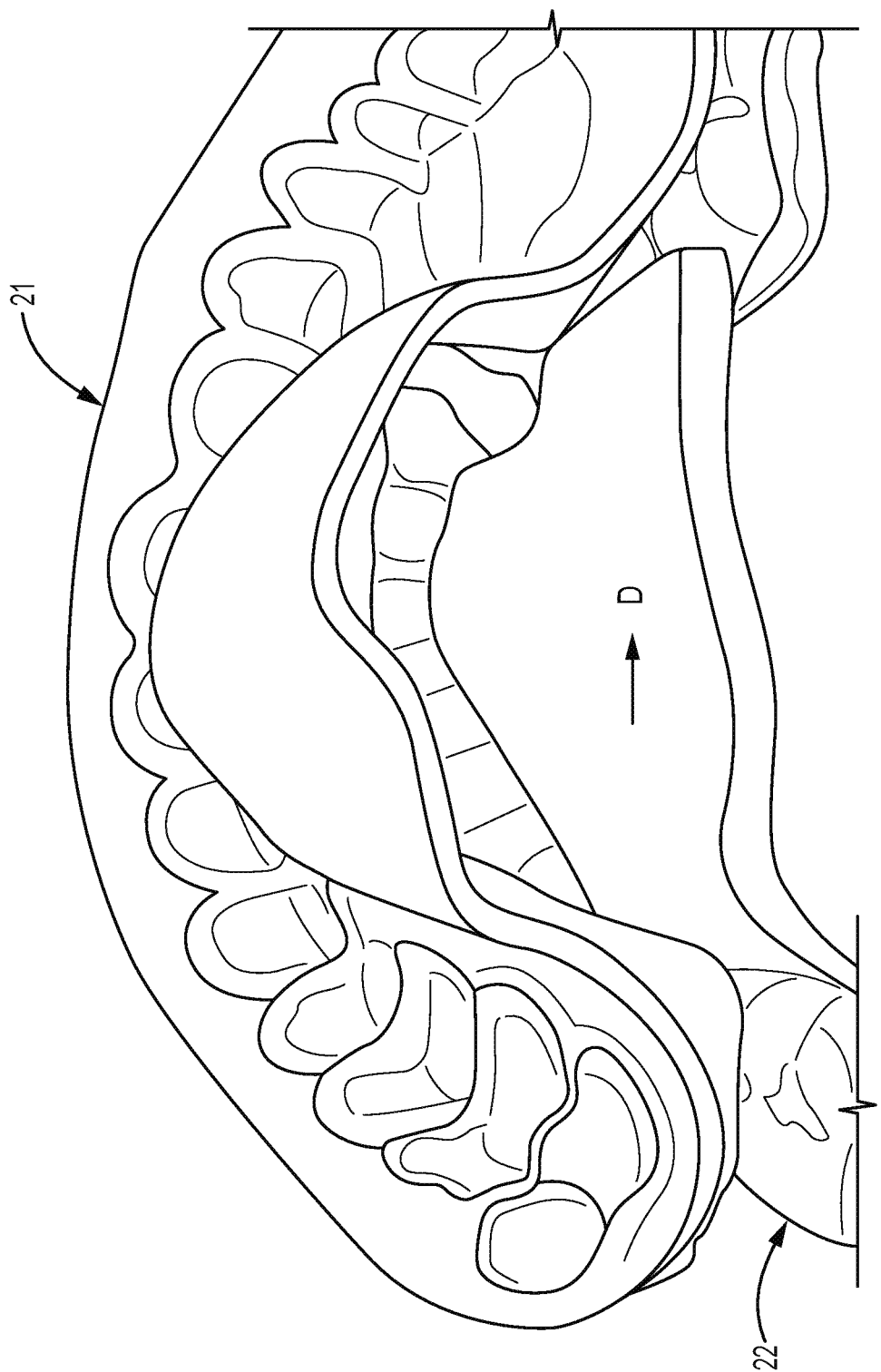
FIG. 9 is a rear view of the second embodiment of the multi-functional oral stent.

As depicted in FIGS. 6-9, a second embodiment of the device is an oral stent comprising three pieces, a first piece 21 corresponding to the upper alveolus that fits over the upper jaw, a second piece 22 corresponding to the lower alveolus to the that fits over the lower jaw, and a flap shaped tongue deviation septum. Each piece can be generally arcuate in shape with curvature matching the shape of the upper and lower rows of teeth, such that the first piece 21 fits over the upper row of teeth by aligning with an upper jaw teeth ridge B in FIG. 7, and the second piece 22 fits over the lower row of teeth by aligning with a lower jaw teeth ridge in FIG. 9, in a patient's jaw. The first piece 11 of the oral stent also includes a reservoir A. Reservoir A can be used to hold a required amount of medication, moisturization liquids, and/or other forms of drugs to be placed therein during treatment. A separator C is also provided between the first piece 21 and the second piece 22 to provide a gap of separation between the two pieces as the point insertion of the separator. In this instance the point of separation is provided at one side of the patient's mouth as shown in FIG. 8 and not in the front as in the first embodiment. And lastly, in this second embodiment, the third piece of the device of the oral stent also includes a flap shaped tongue deviation septum for positioning the tongue inferiorly away from the radiation field during the radiotherapy treatment.

A third aspect of the present subject matter is directed to a method of using the oral stent during radiotherapy treatment. The method uses the multi-functional oral appliance of an oral stent during a radiotherapy treatment of a patient, comprising: applying a required amount of medication, moisturization liquids, and/or other forms of drugs into a reservoir of a first piece of said oral stent; fitting said first piece of the oral stent having an arcuate shape corresponding to the upper jaw of the dental arch of the person such that said first piece fits atop the teeth of the upper jaw line; fitting said second piece of the oral stent having an arcuate shape corresponding to the lower jaw of the dental arch of the person such that said second piece fits atop the teeth of the lower jaw line; providing a separator between said first piece and said second piece where said separator provides a separation space between the first piece and the second piece; and providing a deviation septum to position a tongue away from a radiation field during a radiotherapy treatment and administering the radiotherapy treatment.

It is to be understood that the method and device for providing a multi-functional oral stent during radiotherapy are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A multi-functional oral appliance comprising:
   an oral stent comprising:
      a first piece arcuate in shape and configured to fit over an upper jaw of a patient and configured to correspond to an upper alveolus of the patient, wherein a curvature of the first piece matches a shape of an upper row of teeth of the patient by aligning with an upper jaw teeth ridge of said first piece and wherein the first piece includes a section that is configured to fit over a soft palate of the patient;
      a second piece arcuate in shape and configured to fit over a lower jaw of the patient and configured to correspond to a lower alveolus of the patient, wherein a curvature of the second piece matches a shape of a lower row of teeth of the patient by aligning with a lower jaw teeth ridge of said second piece;
      a reservoir for holding a liquid;
      a deviation septum located on said second piece, wherein said deviation septum is configured to contact a tongue of said patient during a radiotherapy treatment for said patient,
      wherein said first piece and said second piece are spaced apart by a separator situated on a front side of the patient's upper and lower jaw when said first piece is configured to fit over said upper jaw of said patient and said second piece is configured to fit over said lower jaw of said patient, and
      wherein said reservoir is located in said section of said first piece that is configured to fit over the soft palate of the patient.

2. The multi-functional oral appliance as recited in claim 1, wherein said deviation septum has a fin shape.

3. The multi-functional oral appliance as recited in claim 1, said deviation septum has a flap shape that is configured to position said patient's tongue inferiorly away from a radiation field of said radiotherapy treatment.

4. The multi-functional oral appliance as recited in claim 1, wherein said liquid comprises an amount of one or more medications, moisturization liquids, and other forms of drugs to be placed therein during treatment such that a function of the multi-functional oral appliance is selected in accordance with the amount of said one or more medications, said moisturization liquids, and said other forms of drugs placed in said reservoir.

5. The multi-functional oral appliance as recited as recited in claim 1, wherein a height of the oral stent ranges from about 1 cm to about 3 cm.

6. The multi-functional oral appliance as recited as recited in claim 1, wherein the oral stent is made of a material selected from the group consisting of: acrylic resin, poly (methyl methacrylate), polyurethane, co-polymers of vinyl acetate or ethylene, polyvinyl acetate-polyethylene, ethylene vinyl acetate (EVA) copolymer, polyvinylchloride, latex rubber, silicon rubber, laminated or non-laminated thermoplastics, and a combination thereof.

7. A method of using the oral stent of claim 1 during a radiotherapy treatment of a patient, the method comprising:
   applying a required amount of one or more medications, moisturization liquids, and other forms of drugs into a reservoir of the first piece of said oral stent;

fitting said first piece of the oral stent having an arcuate shape corresponding to the upper jaw of the dental arch of the person such that said first piece fits atop the teeth of the upper jaw line;
fitting said second piece of the oral stent having an arcuate shape corresponding to the lower jaw of the dental arch of the person such that said second piece fits atop the teeth of the lower jaw line;
providing a separator between said first piece and said second piece where said separator provides a separation space between the first piece and the second piece;
providing a deviation septum to position a tongue of the patient away from a radiation field during the radiotherapy treatment; and
administering the radiotherapy treatment.

* * * * *